(12) United States Patent
Lee et al.

(10) Patent No.: US 10,675,228 B2
(45) Date of Patent: Jun. 9, 2020

(54) SKIN MASSAGE GEL AND METHOD OF PREPARING THE SAME

(71) Applicants: Guk Hee Lee, Seoul (KR); Geon Guk Han, Seoul (KR)

(72) Inventors: Guk Hee Lee, Seoul (KR); Geon Guk Han, Seoul (KR)

( * ) Notice: Subject to any disclaimer, the term of this patent is extended or adjusted under 35 U.S.C. 154(b) by 0 days.

(21) Appl. No.: 16/010,816

(22) Filed: Jun. 18, 2018

(65) Prior Publication Data

US 2018/0369085 A1    Dec. 27, 2018

(30) Foreign Application Priority Data

Jun. 23, 2017 (KR) .................. 10-2017-0080049

(51) Int. Cl.
| | |
|---|---|
| *A61K 36/00* | (2006.01) |
| *A61K 8/19* | (2006.01) |
| *A61Q 19/00* | (2006.01) |
| *A61K 8/98* | (2006.01) |
| *A61K 8/96* | (2006.01) |
| *A61K 8/9794* | (2017.01) |

(52) U.S. Cl.
CPC ............ *A61K 8/19* (2013.01); *A61K 8/965* (2013.01); *A61K 8/9794* (2017.08); *A61K 8/988* (2013.01); *A61Q 19/00* (2013.01); *A61K 2800/28* (2013.01); *A61K 2800/805* (2013.01); *A61K 2800/85* (2013.01)

(58) Field of Classification Search
None
See application file for complete search history.

(56) References Cited

U.S. PATENT DOCUMENTS

| | | | | |
|---|---|---|---|---|
| 2008/0063690 | A1* | 3/2008 | Chevaux .................. | A23G 1/44 424/440 |
| 2011/0257259 | A1* | 10/2011 | Schmitz .................. | A23G 1/44 514/456 |
| 2013/0296419 | A1* | 11/2013 | Chevaux .................. | A23G 1/44 514/456 |

FOREIGN PATENT DOCUMENTS

| | | |
|---|---|---|
| JP | 2008-007442 A | 1/2008 |
| KR | 10-2006-0015920 A | 2/2006 |
| KR | 10-0753310 B1 | 8/2007 |
| KR | 10-2008-0098967 A | 11/2008 |
| KR | 10-2011-0119358 A | 11/2011 |
| KR | 10-1206985 B1 | 11/2012 |
| KR | 10-1397644 B1 | 5/2014 |

\* cited by examiner

*Primary Examiner* — Michael Barker
*Assistant Examiner* — Randall Winston
(74) *Attorney, Agent, or Firm* — Korus Patent, LLC; Seong Il Jeong

(57) ABSTRACT

The present invention relates to a skin massage gel which does not cause skin irritation because it does not contain dark brown sugar crystals and which can be safely used because it includes only natural materials, and a method of preparing the same. The method includes the steps of: (1) adding 8-12 parts by weight of malt powder made from dehusked malt to 100 parts by weight of rice wine, followed by heating while stirring in one direction; (2) filtering the heated solution using a filter; (3) adding 80-120 parts by weight of dark brown sugar to the filtered solution, followed by heating while stirring; (4) adding 25-35 parts by weight of honey to the solution, followed by heating; (5) adding 0.004-0.006 parts by weight of gold powder to the solution, followed by heating; and (6) aging the solution at room temperature.

1 Claim, 1 Drawing Sheet

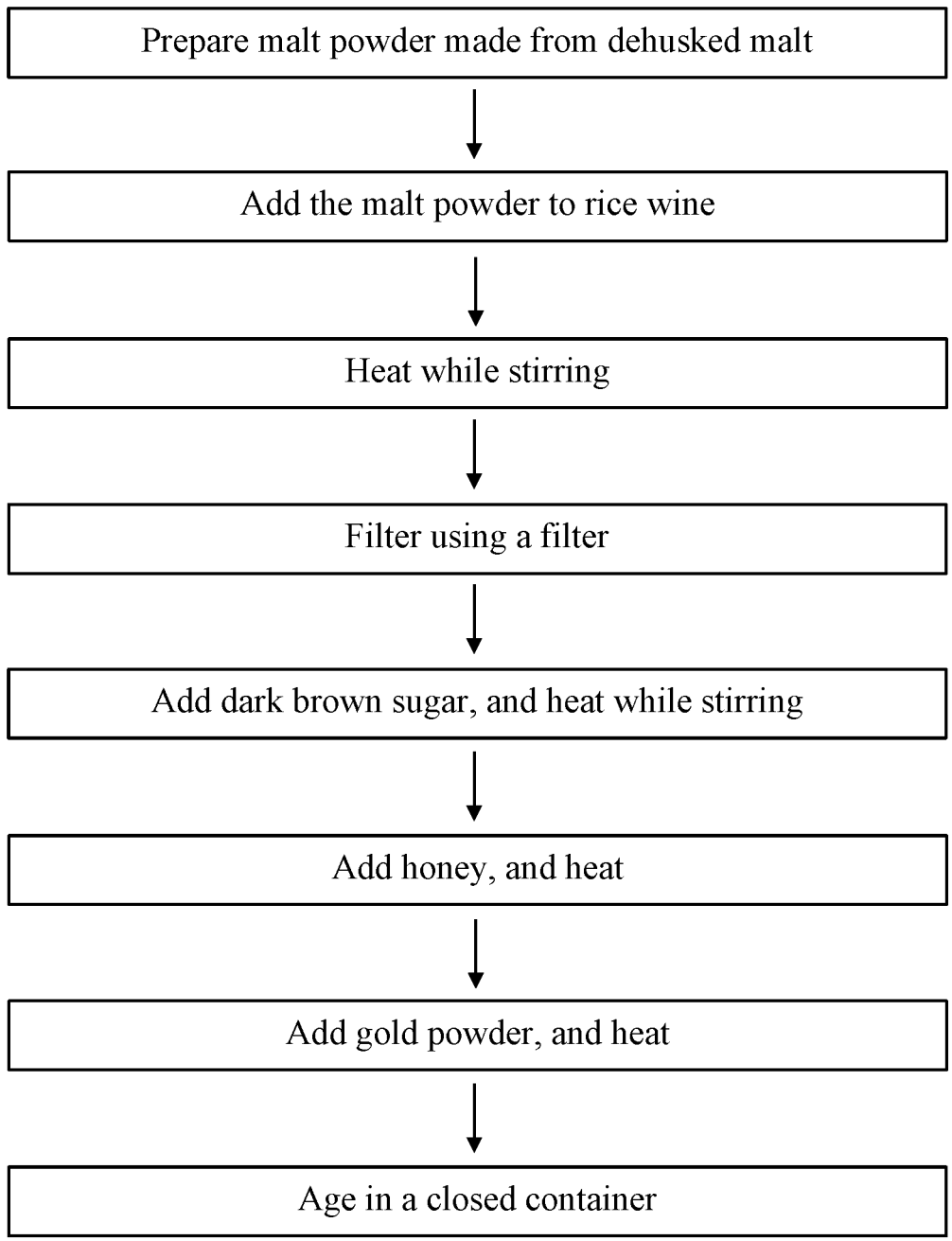

SKIN MASSAGE GEL AND METHOD OF PREPARING THE SAME

BACKGROUND

1. Technical Field

The present invention relates to a skin massage gel and a method of preparing the same, and more particularly to a skin massage gel which does not cause skin irritation because it does not contain dark brown sugar crystals and which can be safely used because it includes only natural materials, and a method of preparing the same.

2. Description of the Related Art

The epidermis, i.e., the outermost layer of the skin, has a substantial barrier against various skin stimuli and acts to maintain the moisture content in the skin at a constant level. To effectively perform the above action, a certain amount of stratum corneum should be present in the outermost layer of the epidermis.

Stimuli of the skin are diverse, and examples thereof include natural stimuli such as strong wind, intense heat, intense cold and the like, which are seasonal atmospheric characteristics, and environmental stimuli such as air pollutants, acid rain, UV rays and the like. These stimuli can be classified into physical stimuli and chemical stimuli. A representative barrier against these stimuli is a barrier in the amount of the stratum corneum.

In the formation of keratin in the skin, generally, new cells travel slowly from the lowest layer of the epidermis to the outermost layer of the epidermis, and then exfoliate from the epidermal layer after a certain period of time. This is called keratinization. However, in modern society, due to hormonal abnormalities caused by excessive stress and sudden changes in external environments, the effects of air pollutants or UV rays that surpass the skin's defense barrier prevent the dead cells of the stratum corneum from exfoliating in normal cycles. Alternatively, due to irregularity in the cycle in which the dead cells exfoliate, the skin tone changes and the skin looks rough and dull. In addition, when makeup is applied, the makeup looks uneven due to uneven stratum corneum and looks cakey.

To solve these problems, many consumers use exfoliant cosmetics which are roughly classified into: cosmetics containing alpha-hydroxy acid (AHA), beta-hydroxy acid (BHA) or the like that chemically remove dead skin cells; and cosmetics containing scrubs that physically remove dead skin cells.

Scrubs that are generally frequently used include artificial scrubs such as polyethylene scrubs, and natural scrubs made by grinding walnut shells or the seeds of fruits such as peach or apricot. These scrubs are an advantage in that various kinds of scrubs can be made by controlling the size and shape thereof during making thereof. However, when these scrubs enter the eye during use, they are not easy to remove, and cause considerable pain and foreign body sensation in the eyeball, and may also cause serious damage to the eyeball if the eye is rubbed during removal of the scrubs. Due to these problems, precautions for use of general scrub products generally include the sentence "please be careful so that will not enter the eye during use. When the scrub enters the eye, please wash out the scrub with running water without rubbing the eye, and when the scrub remains in the eye even after washing, please consult a specialist." Despite such precautions, when a scrub is actually applied to the eye rim, it sometimes enters the eye. In this case, the scrub is not easily washed out, and there is a fatal disadvantage in that irritation of the eyeball cannot be avoided, even when the scrub is removed.

Furthermore, users commonly want cosmetic products that exhibit sufficient moisturizing effects after use thereof. However, in fact, most of commercially available cosmetic products do not satisfy this demand.

In addition, regarding recent market trends of peeling products, well-being trends and at-home peeling products have become popular. Accordingly, even in the future, there will be a need for safe peeling products including natural scrubs.

PRIOR ART DOCUMENTS

Patent Documents (Patent Document 1) KR10-1397644 B
(Patent Document 2) KR10-1206985 B
(Patent Document 3) KR10-2006-0015920 A
(Patent Document 4) KR10-2008-0098967 A

SUMMARY

The present invention has been conceived to overcome the above-described problems, and an object of the present invention is to provide to provide a skin massage gel which does not cause skin irritation because it is prepared using only natural materials and which effectively melts out sebum and dead skin cells through soft and safe massage because it does not contain dark brown sugar crystal, and a method of preparing the same.

To achieve the above object, the present invention provides a method of preparing a skin massage gel, including the steps of: (1) adding 8 to 12 parts by weight of malt powder made from dehusked malt to 100 parts by weight of rice wine to obtain a solution, and then heating the solution while stirring in one direction; (2) filtering the heated solution using a filter; (3) adding 80 to 120 parts by weight of dark brown sugar to the filtered solution, followed by heating while stirring; (4) adding 25 to 35 parts by weight of honey to the solution resulting from step (3), followed by heating; (5) adding 0.004 to 0.006 parts by weight of gold powder to the solution resulting from step (4), followed by heating; and (6) placing the solution resulting from step (5) in a container, followed by aging at room temperature.

The heating in step (1) preferably includes performing boiling until boiling, followed by additional heating at a lower temperature.

The stirring in steps (1) and (3) is preferably performed using a wooden spatula.

Step (5) further includes adding 5 to 10 parts by weight of and yam.

The present invention also provides a skin massage gel prepared by the method of the present invention.

BRIEF DESCRIPTION OF THE DRAWINGS

The above and other objects, features and advantages of the present invention will be more clearly understood from the following detailed description taken in conjunction with the accompanying drawings, in which:

FIGURE is a flowchart showing a process for preparing a massage gel according to the present invention.

DETAILED DESCRIPTION

The present invention will be described below in detail.

With increasing interest in skin washing cleansing and cleansing and skin health, hundreds of foam cleansing products and massage products have been marketed. However, among these products, there are little or no products that do not contain materials such as paraben, silicone, mineral oil obtained from petroleum or the like, and benzophenone. In particular, these products are mostly products prepared by adding synthetic resins to exhibit scrub effects, and such products exhibit skin redness and stinging after use in many cases.

In particular, commercially available natural dark brown sugar massage products for removing sebum and dead skin cells can be easily purchased from cosmetic shops or online stores or through overseas direct purchase, but almost all of these products include crystallized dark brown sugar that give a rough stimulus to the skin during massage, thereby causing the skin to suffer from a lot of pain after massage.

Consumers who have experienced massage with dark brown sugar scrub products answered that skin redness sometimes occurred after massage due to skin friction caused by dark brown sugar crystal grains during massage with the dark brown sugar scrub massage products, and that the skin redness portion sometimes felt hot and painful even after a long time, and thus the use of these scrub products in persons with weak skin would be unsuitable.

In addition, these scrub products have disadvantages in that the use of these products in persons with redness on the face with acne or pimples is more unsuitable and these persons suffer from more skin troubles due to dark brown sugar crystals after use.

The inventor of the present invention has developed a new product which is composed of only natural materials, contains no dark brown sugar crystal, and provides soft massage. Accordingly, even when the new product is simply applied to the skin, the gel component thereof easily adsorbs onto the skin and melts out sebum and dead skin cells.

Therefore, the present invention provides a method of preparing a skin massage gel, including the steps of: (1) adding 8 to 12 parts by weight of malt powder made from dehusked malt to 100 parts by weight of rice wine to obtain a solution, and then heating the solution while stirring in one direction; (2) filtering the heated solution using a filter; (3) adding 80 to 120 parts by weight of dark brown sugar to the filtered solution, followed by heating while stirring; (4) adding 25 to 35 parts by weight of honey to the solution resulting from step (3), followed by heating; (5) adding 0.004-0.006 parts by weight of gold powder to the solution resulting from step (4), followed by heating; and (6) placing the solution resulting from step (5) in a container, followed by aging at room temperature.

The heating in step (1) preferably includes performing boiling until boiling, followed by additional heating at a lower temperature. In a preferred embodiment, the heating in step (1) may first be performed at a temperature of 80 to 100° C., and then performed at a temperature of 60 to 70° C.

The stirring in steps (1) and (3) is preferably performed using a wooden spatula. The use of the wooden spatula can effectively prevent the rice wine from overflowing due to boiling.

Step (5) preferably further includes adding 5 to 10 parts by weight of yam. The yam contains a large amount of cellulose, and thus has an excellent effect of removing dead skin cells upon skin massage and can minimize skin irritation.

A method of preparing the skin massage gel according to a preferred embodiment of the present invention is as follows.

First, dehusked malt is placed in a sieve with a fine mesh, and sieved by hand such that powder falls down. When the sieving is continued, fine powder falls down. The sieving is continued until 100 g of malt powder is obtained, thereby preparing fine powder. Then, 100 g of the fine malt powder is added to 1 liter of cold rice wine to obtain a solution. The solution is placed in a large transparent beaker and stirred in one direction by use of a wooden spatula until boiling. The stirring is performed so that the powder will not clump. When the solution boils, bubbles are formed, and even at this time, the solution is carefully stirred in one direction so that it will not overflow. Rice wine boils faster than water due to its lower boiling point and overflows faster because it is a volatile liquid. For these reasons, the time when it boils should be monitored well so that it can be prevented from overflowing. 3 Minutes after the solution starts to boil, the temperature of the flame is reduced by two steps, and the solution is further boiled for 7 minutes. After completion of the boiling, malt particles having a large diameter are filtered out once using a filter or a sieve. 1 kg of dark brown sugar is added slowly to the filtered refined rice wine and dissolved, and then the solution is further boiled for 5 minutes while it is continuously stirred using a wooden spatula. At this time, stirring the solution using the wooden spatula can prevent the loss of the solution because the wooden component prevents the solution from overflowing. If the solution is stirred with a steel scoop or a steel spatula, excessive bubbles are created upon boiling, and ⅓ of the raw material overflows, indicating that the loss of the material is large. After completion of the boiling, 300 g of horny is added to the solution which is then further boiled for about 2 to 3 minutes. 0.05 g of edible gold powder is poured into the boiled solution in such a manner that it does not blow off. Next, the resulting solution is further boiled for 1 to 2 minutes, and then cooled. During the cooling, the lid is closed tightly to block air. When the cooled solution is aged in a closed state at room temperature for 24 hours, a dark brown sugar massage gel which is not crystallized even at room temperature is obtained.

The skin massage gel of the present invention, prepared by the above-described method, is a dark brown sugar massage product in a gel state, and is maintained in the gel state even when it is stored for a long period of time. As described above, even when the skin massage gel is simply applied safely to a sensitive skin or the like, to which conventional dark brown sugar massage products are hardly applied, the dark brown sugar component in a gel state is absorbed into and adsorbed onto the skin and penetrates the epidermis and dermis of the skin, thereby exhibiting the effect of easily removing sebum and dead cells from the skin.

The skin massage gel of the present invention is prepared by dissolving dark brown sugar in 100% rice wine, and thus has the effect of killing skin trouble-causing bacteria, thereby alleviating skin troubles or acne.

Furthermore, the skin massage gel of the present invention does not contain water components other than rice wine, and thus has an advantage in that it does not deteriorate even when it is stored for several years, suggesting that it can be stored for a long period of time even when a separate preservative is not added thereto.

In addition, the skin massage gel of the present invention is prepared by dissolving dark brown sugar and honey in rice wine and adding 24k pure gold to the solution, and thus makes the skin more healthy by skin self-cleaning, skin whitening and shooting, anti-aging, detoxification, freckle relaxation, wrinkle prevention and freckle removal effects, which are the effects of gold, also described in Dongui-bogam (a traditional Korean medical book compiled by Heo Jun in 1613 during the Joseon Dynasty of Korea).

Therefore, the present invention also provides a skin massage gel prepared by the method of the present invention as described above.

In a preferred embodiment, the skin massage gel of the present invention can be washed out after a proper amount of the massage gel is thoroughly applied by hand to a face, hands, a neck or the like through a massage-like method. More preferably, it is washed out 5 to 10 minutes after its application to the skin, and in this case, a skin whitening effect, a skin soothing effect and a sweet pore-reducing effect can be visually seen.

Even when the skin massage gel of the present invention is merely applied to the skin without continuous massage, the gel-state product adsorbs onto the skin and deeply penetrates the skin's epidermis and dermis, thereby melting out dirt, impurities and the like from the skin. In addition, it allows the skin to self-cleanse and forms a protective layer on the skin, so that the skin can be maintained healthy all day long.

In addition, the skin massage gel of the present invention has an advantage in that skin protection and moisturization are maintained all day long without pulling even when only skin softener or lotion is simply used without additionally using a number of cosmetic products after the massage gel is used.

When the skin massage gel of the present invention is applied to a problematic skin (suffering from skin troubles when cosmetic products are applied), a skin with eczema and fever, an atopic skin, or an itchy skin, the skin conditions are significantly improved, the skin is well balanced, and the moisturizing effect is maintained throughout the day, indicating that the skin massage gel have excellent effects.

In other preferred embodiments, the skin massage gel of the present invention may also be used along with various natural powders having skin beauty and soothing effects. For example, the skin massage gel of the present invention may be used as a pack or massage formulation along with pomegranate powder, adlay powder, chestnut powder, green tea powder and the like.

The present invention will be described in more detail below with reference to specific examples. It is to be understood, however, that these examples are intended for illustrative purposes only and are not intended to limit the scope of the present invention.

EXAMPLES

Example 1

First, dehusked malt was placed in a sieve with a fine mesh, and was sieved by hand such that powder fell down, thereby preparing 100 g of fine malt powder. Then, 100 g of the fine malt powder was added to 1 liter of cold rice wine to obtain a solution. The solution was placed in a large transparent beaker and stirred in one direction by use of a wooden spatula until boiling. 3 Minutes after the solution started to boil, the temperature of the flame was reduced by two steps, and the solution was further boiled for 7 minutes. Next, malt particles having a large diameter were filtered out using a filter. 1 kg of dark brown sugar was added slowly to and dissolved in the filtered refined rice wine, and then the solution was further boiled for 5 minutes while it was continuously stirred using a wooden spatula. Next, 300 g of horny was added to the solution which was then further boiled for about 2 to 3 minutes. 0.05 g of edible gold powder was poured into the boiled solution in such a manner that it did not blow off. Next, the resulting solution was further boiled for 1 to 2 minutes, and was then cooled. During the cooling, the lid was closed tightly to block air. Next, the cooled solution was aged in a closed state at room temperature for 24 hours, thereby obtaining a skin massage gel.

Example 2

A skin massage gel was prepared in the same manner as described in Example 1, except that 50 g of yam was further added when the edible gold powder was added.

Comparative Example 1

A commercially available dark brown sugar scrub (manufactured by L company) was used.

Comparative Example 2

A commercially available cleansing foam (manufactured by A company) was used.

Test Example

The products of Examples 1 and 2 and Comparative Examples 1 and 2 were used by 30 adult men and women, and then the performances of the products were evaluated according to a five-point scale as shown in Table 1 below.

TABLE 1

| Samples | Feeling of use | Moistness | Dead skin cell removal effect | Skin irritation | Overall evaluation |
| --- | --- | --- | --- | --- | --- |
| Example 1 | 4.5 | 4.4 | 4.6 | 4.5 | 4.5 |
| Example 2 | 4.6 | 4.6 | 4.8 | 4.6 | 4.7 |
| Comparative Example 1 | 2.7 | 3.0 | 4.4 | 2.5 | 3.0 |
| Comparative Example 2 | 3.3 | 3.2 | 3.1 | 3.5 | 3.2 |

As shown in Table 1 above, the skin massage gel was excellent in terms of the feeling of use, the moistness, the dead skin cell removal effect and the skin irritation compared to the conventional dark brown sugar scrub and cleaning form.

As described above, the skin massage gel obtained according to the preparation method of the present invention is composed of only natural materials that cause no skin irritation, contains no dark brown sugar crystal, and thus can effectively remove sebum and dead cells from the skin without skin-irritating friction. Accordingly, the skin massage gel may be used safely for a sensitive skin, a trouble skin or a weak skin, and thus is an invention which is very useful in the beauty industry.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A method of preparing a skin massage gel, comprising the steps of:
   (1) adding 8 to 12 parts by weight of malt powder made from dehusked malt to 100 parts by weight of rice wine to obtain a solution, and then heating the solution to a temperature in a first temperature range of 80° C. to 100° C. while stirring the solution in one direction, followed by heating the solution at a lower temperature in a second temperature range of 60° C. to 70° C.;
   (2) filtering the heated solution using a filter;
   (3) adding 80 to 120 parts by weight of black dark brown sugar to the filtered solution, followed by heating the solution in the first temperature range while stirring the solution;
   (4) adding 25 to 35 parts by weight of honey to the solution resulting from step (3), followed by heating the solution in the first temperature range;
   (5) adding 0.004 to 0.006 parts by weight of gold powder and 5 to 10 parts by weight of yam to the solution resulting from step (4), followed by heating the solution in the first temperature range; and
   (6) placing the solution resulting from step (5) in a container, followed by aging at room temperature for a predetermined time period, thereby changing the solution to a gel state.

* * * * *